United States Patent [19]

Smith

[11] 4,164,502

[45] Aug. 14, 1979

[54] 2-DECARBOXY-2-AMINOMETHYL-TRANS-4,5,13,14-TETRADEHYDRO-PGI$_1$ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 915,429

[22] Filed: Jun. 14, 1978

Related U.S. Application Data

[63] Continuation-in-part of Ser. No. 821,536, Aug. 3, 1977.

[51] Int. Cl.$^2$ ............................................. C07D 307/93
[52] U.S. Cl. ................................................ 260/346.73
[58] Field of Search ..................................... 260/346.73

[56] References Cited

PUBLICATIONS

Johnson et al., J.A.C.S., 9:12, Jun. 1977, pp. 4182–4184.

*Primary Examiner*—John M. Ford
*Assistant Examiner*—Bernard Dentz
*Attorney, Agent, or Firm*—Robert A. Armitage

[57] ABSTRACT

The present invention relates to certain structural and pharmacological analogs of prostacyclin (PGI$_2$) which are 2-Decarboxy-2-aminomethyl-trans-4,5,13,14-tetradehydro-PGI$_1$ compounds. These novel pharmacological agents are useful as smooth muscle stimulators.

27 Claims, No Drawings

2-DECARBOXY-2-AMINOMETHYL-TRANS-4,5,13,14-TETRADEHYDRO-PGI₁ COMPOUNDS

CROSS REFERENCE TO RELATED APPLICATION

The present application is a continuation-in-part of Ser. No. 821,536, filed Aug. 3, 1977, now pending.

The present invention relates to prostacyclin analogs, for which the essential material constituting disclosure therefor is incorporated by reference here from Ser. No. 821,541, filed Aug. 3, 1977, now U.S. Pat. No. 4,109,082, issued Aug. 22, 1978.

I claim:

1. A prostacyclin analog of the formula

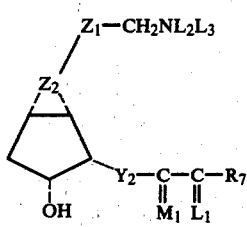

wherein $Y_2$ is -C≡C-;
wherein $Z_2$ is

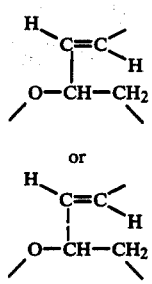 (1)

or (2)

wherein $Z_1$ is
(1)-$(CH_2)_g$-$CH_2$-$CH_2$-, or
(2)-$(CH_2)_g$-$CH_2$-$CF_2$-,
wherein g is the integer zero, one, or 2;
wherein $M_1$ is

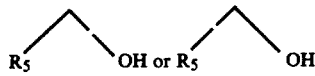

wherein $R_5$ is hydrogen or alkyl with one to 4 carbon atoms, inclusive; and
wherein $L_1$ is

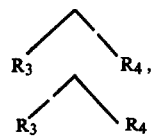

or a mixture of

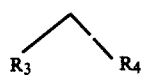

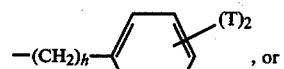

wherein $R_3$ and $R_4$ are hydrogen, methyl, or fluoro, being the same or different, with the proviso that one of $R_3$ and $R_4$ is fluoro only when the other is hydrogen or fluoro;
wherein $L_2$ and $L_3$ are hydrogen or alkyl of one to 4 carbon atoms, inclusive; and
wherein $R_7$ is
(1)-$(CH_2)_m$-$CH_3$,

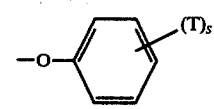 (2)

, or (3)

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl; and the pharmacologically acceptable acid addition salts thereof.

2. A prostacyclin analog according to claim 1, wherein $Z_2$ is a mixture of

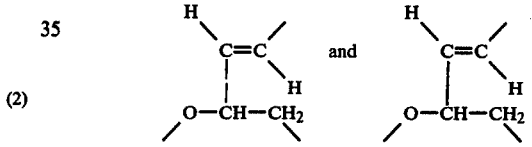

3. 2-Decarboxy-2-aminomethyl-(6RS)-trans-4,5,13,14-tetrahydro-PGI₁, a prostacyclin analog according to claim 2.

4. A prostacyclin analog according to claim 1, wherein $Z_2$ is

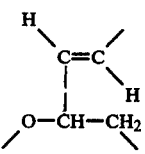

5. 2-Decarboxy-2-aminomethyl-trans-4,5,13,14-tetradehydro-6α-PGI₁, a prostacyclin analog according to claim 4.

6. 2-Decarboxy-2-aminomethyl-15-methyl-trans-4,5,13,14-tetradehydro-6α-PGI₁, a prostacyclin analog according to claim 4.

7. 2-Decarboxy-2-aminomethyl-16,16-dimethyl-trans-4,5,13,14-tetradehydro-6α-PGI₁, a prostacyclin analog according to claim 4.

8. 2-Decarboxy-2-aminomethyl-16,16-difluoro-trans-4,5,13,14-tetradehydro-6α-PGI₁, a prostacyclin analog according to claim 4.

9. A prostacyclin analog according to claim 1, wherein $Z_2$ is

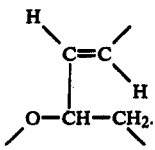

10. A prostacyclin analog according to claim 9, wherein $Z_1$ is -(CH$_2$)$_g$-CH$_2$-CF$_2$-.

11. 2-Decarboxy-2-aminomethyl-2,2-difluoro-trans-4,5,13,14-tetradehydro-6β-PGI$_1$, a prostacyclin analog according to claim 10.

12. A prostacyclin analog according to claim 9, wherein $Z_1$ is -(CH$_2$)$_g$-CH$_2$-CH$_2$-.

13. A prostacyclin analog according to claim 12, wherein g is zero.

14. A prostacyclin analog according to claim 13, wherein $R_7$ is

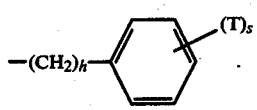

15. 2-Decarboxy-2-aminomethyl-17-phenyl-18,19,20-trinor-trans-4,5,13,14-tetradehydro-6β-PGI$_1$, a prostacyclin analog according to claim 14.

16. A prostacyclin analog according to claim 13, wherein $R_7$ is

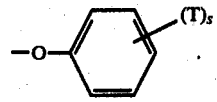

17. 2-Decarboxy-2-aminomethyl-16-phenoxy-17,18,19,20-tetranor-trans-4,5,13,14-tetradehydro-6β-PGI$_1$, a prostacyclin analog according to claim 16.

18. A prostacyclin analog according to claim 13, wherein $R_7$ is -(CH$_2$)$_m$-CH$_3$-.

19. A prostacyclin analog according to claim 18, wherein $R_5$ is methyl.

20. 2-Decarboxy-2-aminomethyl-15-methyl-trans-4,5,13,14-tetradehydro-PGI$_1$, a prostacyclin analog according to claim 19.

21. A prostacyclin analog according to claim 18, wherein $R_5$ is hydrogen.

22. A prostacyclin analog according to claim 21, wherein at least one of $R_3$ and $R_4$ is fluoro.

23. 2-Decarboxy-2-aminomethyl-16,16-difluoro-trans-4,5,13,14-tetradehydro-6β-PGI$_1$, a prostacyclin analog according to claim 22.

24. A prostacyclin analog according to claim 21, wherein at least one of $R_3$ and $R_4$ is methyl.

25. 2-Decarboxy-2-aminomethyl-16,16-dimethyl-trans-4,5,13,14-tetradehydro-6β-PGI$_1$, a prostacyclin analog according to claim 24.

26. A prostacyclin analog according to claim 21, wherein $R_3$ and $R_4$ are both hydrogen.

27. 2-Decarboxy-2-aminomethyl-trans-4,5,13,14-tetradehydro-6β-PGI$_1$, a prostacyclin analog according to claim 26.

* * * * *